United States Patent [19]
Johansen et al.

[11] Patent Number: 5,177,509
[45] Date of Patent: Jan. 5, 1993

[54] ULTRAVIOLET RADIATION AND BLUE LIGHT BLOCKING POLARIZING LENS

[75] Inventors: Laurie A. Johansen; Paul A. Diffendaffer, both of LaCrescenta, Calif.

[73] Assignee: Suntiger, Inc., North Hollywood, Calif.

[21] Appl. No.: 421,083

[22] Filed: Oct. 13, 1989

Related U.S. Application Data

[63] Continuation of Ser. No. 329,600, Mar. 28, 1989, Pat. No. 4,878,748, which is a continuation-in-part of Ser. No. 19,556, Feb. 26, 1987, abandoned.

[51] Int. Cl.$^5$ ............................ G02C 7/10; G02C 7/12
[52] U.S. Cl. ......................................... 351/44; 351/49
[58] Field of Search ...................... 351/44, 47, 48, 49, 351/163; 350/438; 359/361

[56] References Cited

U.S. PATENT DOCUMENTS

| | | |
|---|---|---|
| 2,370,697 | 3/1945 | Tillyer . |
| 4,043,637 | 8/1977 | Hovey . |
| 4,952,046 | 8/1990 | Stephens et al. . |

FOREIGN PATENT DOCUMENTS

| | | |
|---|---|---|
| 2307602 | 8/1974 | Fed. Rep. of Germany . |
| 1114996 | 7/1954 | France . |
| 2236479 | 2/1975 | France . |
| 8100769 | 3/1981 | PCT Int'l Appl. . |

OTHER PUBLICATIONS

Hadmon Inc, "Model 112 Safety Goggles sharpen viewing in Ultraviolet radiation Field"–1968.
Emsley "Filters: Absorptive And Thin Film" The Optician vol. 137 No 3559, Jun. 19, 1959.

*Primary Examiner*—Rodney B. Bovernick
*Attorney, Agent, or Firm*—Pretty, Schroeder, Brueggemann & Clark

[57] ABSTRACT

A lens (10) that substantially blocks horizontally polarized light and selectively blocks wavelengths between 300 and 549 nanometers. The selective blocking is controlled by a sharp cut-on filter (14) selected to cut-on at either 450, 500, 515, 530, or 550 nanometers. The specific blocking and cut-on point selected is dependent upon the ultimate usage/environment of the lens (10). If a 450 cut-on filter is selected, wavelengths between 300 and 449 nanometers are blocked before a cut-on occurs at 450 nanometers; similarly, a 550 cut-on filter blocks wavelengths between 300 and 549 nanometers before a cut-on occurs at 550 nanometers. The lens (10) also allows 30 to 40 percent of wavelengths over 625 nanometers to be transmitted. The filter (14) in combination with the polarizer (16) blocks harmful Ultraviolet radiation and blue light. While a beneficial and calming effect is achieved by wearing only blue-blocking lenses, the addition of the polarizer (16) substantially enhances the calming effect and the improvement of vision without visual discomfort.

16 Claims, 5 Drawing Sheets

BEST MODE TABLE

| WAVE LENGTH OF FILTER CUT-ON (nm) | TIME IN COMBINATION DYE AT 98°C AND 0.25gm/LITER CONCENTRATION SIDNEY SPRINGER DYE CO. LOS ANGELES, CA. | | | RECOMMENDED USES | |
|---|---|---|---|---|---|
| | DISPENSED YELLOW 23 | DISPENSED ORANGE 3 | DISPENSED RED 2 | ENVIRONMENTS | ACTIVITY |
| 450 | 2.5 MINUTES | | | TRAFFIC | ACTIVITIES REQUIRING COLOR VERITY |
| 500 | 5.0 MINUTES | | | AQUATIC | LIFE GUARD |
| 515 | 12.0 MINUTES | | | TRAFFIC | BOATER |
| 530 | | 4.5 MINUTES | | AQUATIC | DRIVING REQUIRING STOP LIGHT VERITY |
| 550 | | 12.0 MINUTES | | AQUATIC | FISHING |
| 515 TO 550 | AS INDICATION ABOVE | | | HIGH ALTITUDE | PILOT |

FIG. 3

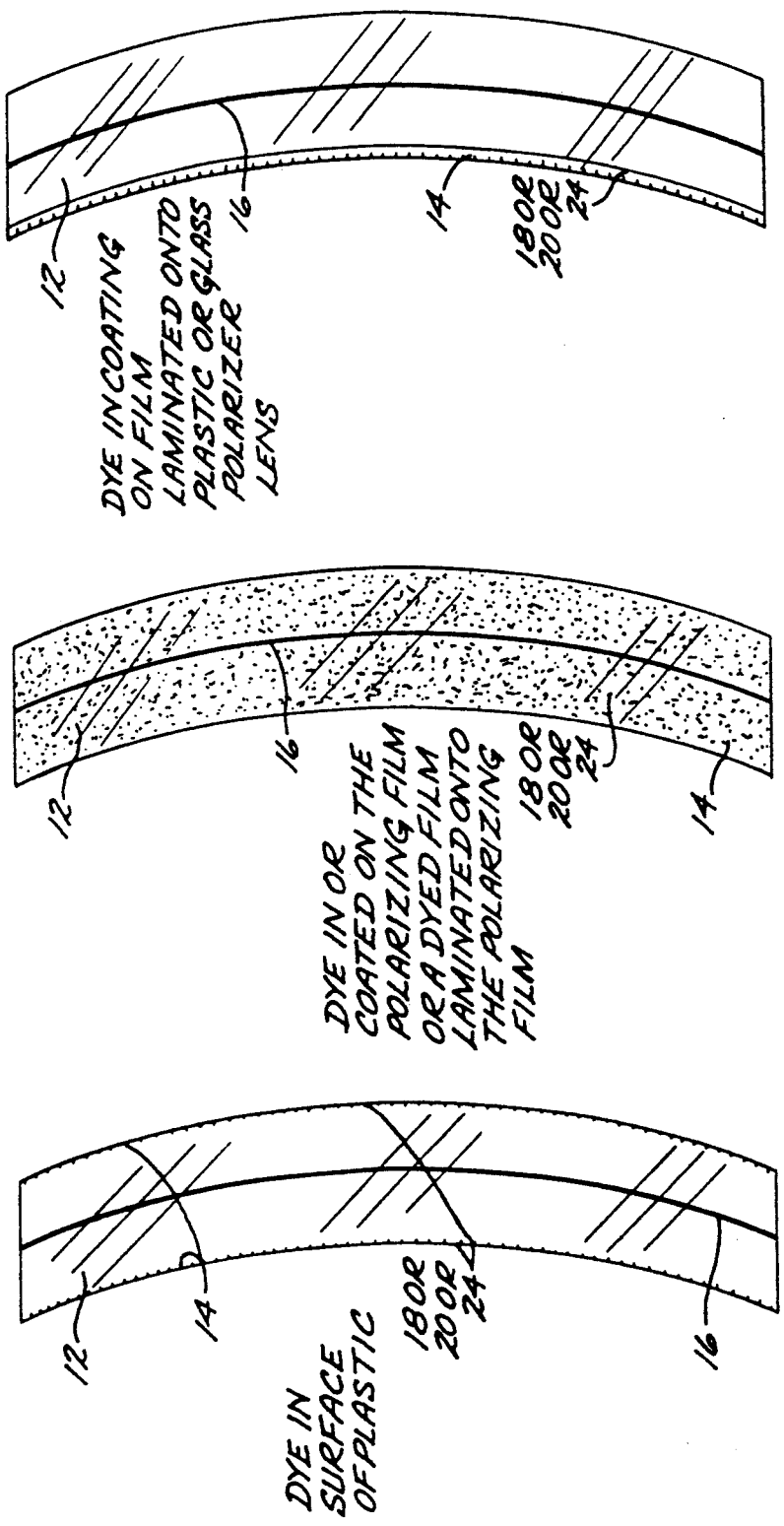

ULTRAVIOLET RADIATION AND BLUE LIGHT BLOCKING POLARIZING LENS

CROSS REFERENCE TO RELATED APPLICATION

This application is a continuation of application Ser. No. 329,600, filed on Mar. 28, 1989 and thereafter issued as U.S. Pat. No. 4,878,748, which is itself a continuation-in-part of application Ser. No. 07/019,556 filed on Feb. 26, 1987 and thereafter abandoned. Application Ser. No. 07/019,556 is based on an international application, U.S. 86/02213, which was filed on Oct. 16, 1986 and designates the United States of America as well as other countries.

TECHNICAL FIELD

The invention pertains to the general field of sunglass lenses and more particularly with lenses that combine a polarizer that blocks horizontally polarized light and a sharp cut-on filter that blocks blue light and ultraviolet radiation.

BACKGROUND ART

It is well known that energy radiated in the form of light is capable of inducing and/or promoting certain photochemical reactions and that different photochemical reactions are induced by the action of light rays (or photons) of various wavelengths. Certain wavelengths of light, especially those in the blue and ultraviolet range, are known to be injurious to the eye.

Dyed lenses, when used with prescription or non-prescription sunglasses are basically intended to fulfill one of two functions: the first function is either selective or overall reduction of the injurious light and radiation. Lenses dyed for this purpose are known as protective lenses. Protective lenses may block harmful wavelengths either by reflection or, more commonly, by absorption. The second function is fulfilled by lenses which fulfill cosmetic requirements and are referred to as fashion tints. Combination dyes covering both requirements are also available.

In the current art, there are protective lenses that block blue and ultraviolet wavelengths and there are separate polarizing lenses that block horizontally polarized incident light. The combination of a polarizing and a blue and ultraviolet blocking lens is not currently available as confirmed by a listing of lenses published in 1986 by Retinitis Pigmentosa International and a search of the advertising literature. The non-availability of these combination lenses is due, in part, to the little research that has been conducted by sunglass companies on the detrimental effect of the blue light harzard to the retina of the eye and the technical problems encountered in combining the temperature-sensitive polarizing film with the dye. This problem has been solved by the instant invention by selecting dyes that can provide the required blue blocking at a temperature that will maintain the usefulness and structural integrity of the polarizing film.

A search of the prior art did not disclose any patents that read directly on the claims of the instant invention. However, the following U.S. and foreign patents were considered related:

| PATENT NO. | INVENTOR | ISSUED |
| --- | --- | --- |
| 4,261,656 | Shy-Hsien Wu | 14 April 1981 |
| 2,307,602 (DE) | Krumeich | 29 August 1973 |
| 3,588,216 | Bloom | 28 June 1971 |
| 3,460,960 | Francel et al | 12 August 1969 |
| 2,643,982 | Riley | 30 June 1953 |

The Shy-Hsien Wu patent discloses a transparent, optically clear article that consists of a glass or plastic base element that supports a thin and delicate organic or inorganic surface film such as a plastic polarizing film. The film is protected from the damaging effects of moisture, scratching and abrasion by a protective plastic coating. The hardness of the protective coating is controlled to avoid excessive flexibility or brittleness, so that good scratch resistance over a relatively soft film is obtained.

The Krumeich German Offenlegungsschrift discloses an optical filter that corrects red/green color blindness. The filter is designed so that in the blue to green range of the visible spectrum, the spectra curve progresses at a constant rate at very low values and increases steeply to a high value in the green to red range. The filter is particularly advantageous if its spectra curve has a permeability of under 0.01 percent in the blue to green range and a transmission that increases to approximately 100 percent in the red range.

The Bloom patent discloses an element for filtering infrared light. A metal complex is employed as an infrared absorber in which the metal is a metal of the first, second or third transition metal series which will provide a complex that is an effective infrared absorber and which is effectively transparent to light in the visible region of the spectrum.

The Francel et al. patent discloses a method of coating a vitreous substrate, such as glass, with a fluid coating composition. The coating imparts to an otherwise clear and/or transparent glass substrate the light transmittance characteristic of amber or darker glass. The simulated amber glass obviates the necessity of having separate amber glass, batch-melting and auxiliary manufacturing apparatus and related equipment.

The Riley patent discloses an absorbent liquid coating composition that forms a film that is applied as a protective and/or decorative coating to glass and other normally transparent or translucent materials. The film has the properties of absorbing substantially all the wavelengths of ultraviolet, violet and blue light below approximately 490 nanometers and substantial amounts of wavelengths from 630–750 nanometers. The film allows the transmission of selected wavelengths above 490 nanometers.

BRIEF DESCRIPTION OF DRAWINGS

FIG. 3 is a table that lists the various combination dyes, the time and temperature required to provide the specific cut-on wavelengths desired and the recommended uses for the lens.

FIG. 5 is a cross-section of a lens showing the dye absorbed into the surface of the plastic and a polarizing film laminated between the two halves of the cast or preformed plastic lens.

FIG. 6 is a cross-section of a lens showing the dye in the body of the plastic and a polarizing film laminated between the two halves of the cast or preformed plastic lens.

FIG. 7 is a cross-section of a lens having a laminated polarizing film and a dye that is in a coating or a laminated film that is bonded to the inside or outside of the lens.

DISCLOSURE OF THE INVENTION

Figure 1:
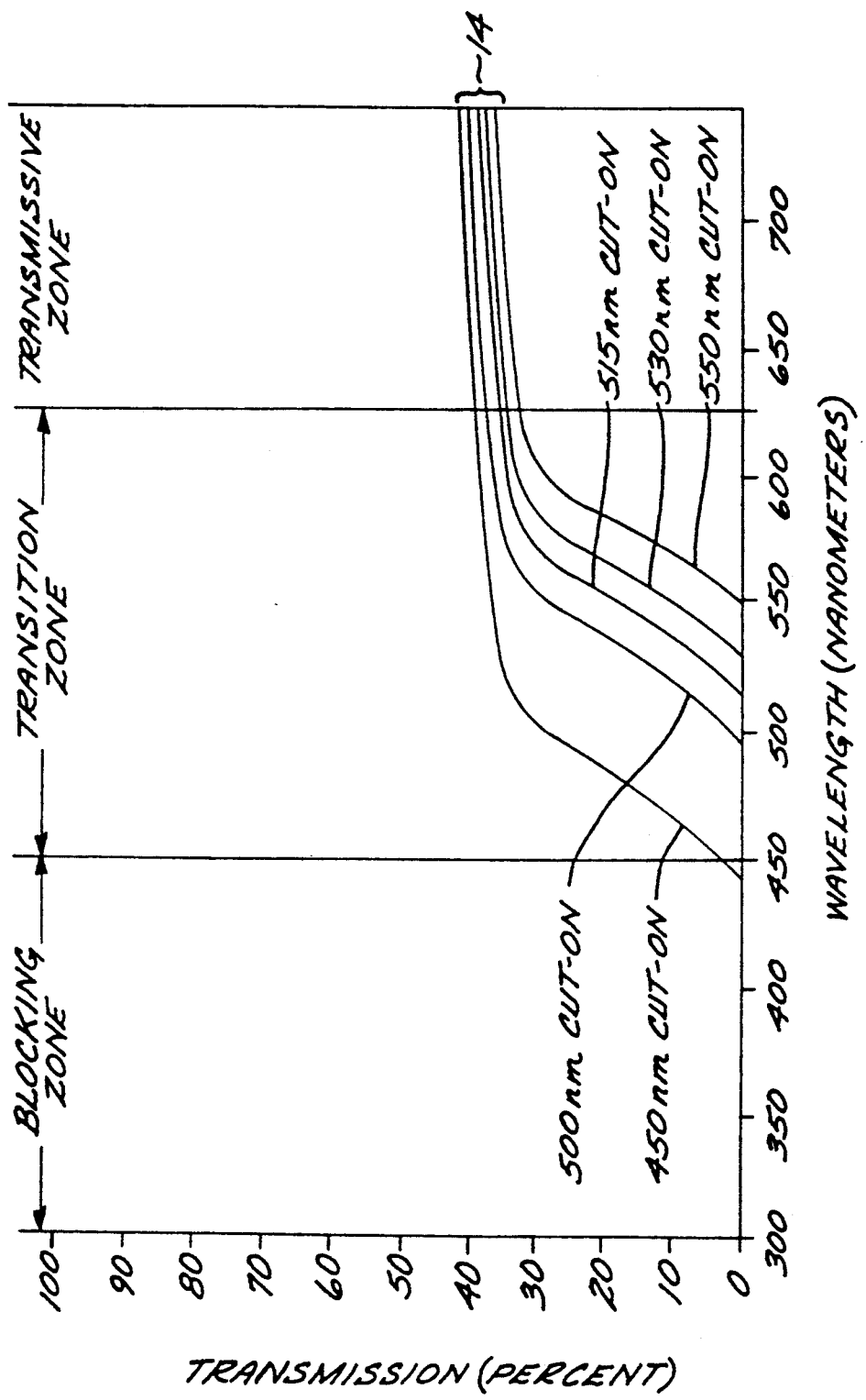
FIG. 1 is a graph that shows the five spectral curves of the invention and the position of each curve within a blocking zone, a transition zone and a transmissive zone.

The ultraviolet radiation and blue light blocking polarizer lens is designed primarily for use with sunglasses to block horizontally polarized light, to selectively block selected wavelengths from 300 to 549 nanometers and to pass 30 to 40 percent of wavelengths longer than 625 nanometers. The selective blocking is controlled by a sharp cut-on filter selected to cut-on at either 450, 500, 515, 530, or 550 nanometers. The atmosphere blocks wavelengths that are shorter than 300 nanometers. Therefore, only wavelengths longer than 300 nanometers need be blocked for safety.

Sunglasses are normally made for light or dark conditions and it is customary to have one or two pairs of sunglasses—one for overcast days and another for sunny days. The inventive lenses found to be usable over a wide range of lighting conditions from dark rainy days to brilliant desert sun. This unexpected usefulness, under such a wide range of light conditions, is thought to be caused by a psychophysiological (or photo-neurologic) effect resulting from the reduction of high intensity stimulation in local areas of the visual field in conjunction with the removal of the blue light stimulation.

Another important and unexpected advantage of the inventive lens is the strong improvement in vision provided in bright light without discomfort to the eye. In other words, the user simultaneously sees very clearly with no discomfort from this intensely clear vision. It is hypothesized that this phenomenon is also a result of a photo-neurologic or psychophysical response to the removal of blue light and high intensity glints reflected into localized areas in the visual field.

The removal of these glints and blue light appear to act synergistically to change the behavior of the retina resulting in the increased visual sensitivity and inducing a calming effect to the user. The inclusion of a polarizer substantially enhances the calming effect. It is again hypothesized that the removal of the high intensity areas of the visual field affects the neural response to the light and thus increases the calming effect of the blue blocking alone.

A general trait of sensory systems is that the sensitivity of the system to information input is affected by the intensity of the stimuli presented to it. In the case of the eye, damage is principally caused by intense exposure to short wavelength radiation. In the case of a visual field where there is a diffusely illuminated area and a specular reflection of the sun in that area, the retina is most sensitive to damage from the contribution of the specular portion.

The eye is able to see over a wide range of lighting conditions by changing the sensitivity of the retina as a function of the light input and by changing the diameter of the pupil. The settings for these factors are in part based on a tradeoff between a need for safety to the retina and the need to see well. Since the specular sources are disproportionately effective in causing damage to the retina, it is reasonable to hypothesize that specular sources would be disproportionately effective in supplying sensitivity settings to the retina. The cellular site for this effect could be Ricco's area in the ganglion cell receptive field center since it is known to be involved in setting the gain of receptor cells in the retina for simple brightness. Accordingly, the wavelength (or blueness) of a specular source, and the intensity of a specular source should enter into the control of the information handling of the retina and the apparent result is referred to as the "blue-glint retinal response." This effect was unknown before the reduction to practice of the instant invention.

Information processing in the eye enters into many neurological responses in the brain. In particular, the eye supplies information which sets neuroendocrine levels appropriate to sleep and alertness. It has also been suggested that light level and spectral composition enter into seasonal behavior patterns involved in mood and sex hormone levels. Since the blue-glint information processing response allows the blue, high intensity light to be disproportionately effective in stimulating sensitivity responses, it may also be involved in the calming effect which is far beyond that noted from blue blocking lenses alone. The effect of the blue glint removal may not be limited to the retina, but may also have a psycho-physical effect on the brain. The brain may be affected as a result of the blue-glint retinal response, thereby affecting mood and instilling the observed calming effect.

This blue glint phenomenon may have evolved in response to the particular damaging effects of high intensity blue light on the retina. There is a theory of retinal radiation damage involving the concept of daily damage accumulation and of renewal mechanisms that repair the damage by removing and replacing the damaged molecules and structures or cells. In addition, by-products of the renewal process (amino acid sequencing defects in proteins and the formation of other nondegradable molecular debris such as lipofuscin) can also accumulate resulting in impaired cell function. Under this theory, the retinal cells progressively accumulate damage, and when damage rates are higher due to harmful chemical or radiation exposure, the accumulation of damage is also higher.

Superimposed upon this general increase in debris from the renewal process in the retina, there are shorter term accumulations of damage which occur during light exposure during the day which is then removed and replaced overnight. However, the renewal mechanisms have finite rates of repair, and if the light exposure is over a certain point, the renewal processes overnight are insufficient to bring the retina back to close to its previous state by morning. This damage is similar to the progressive accumulation of damage described above, and contributes to it, but it is in addition to this progressive accumulation of damage, and affects the function of the eye on a shorter time scale. An example of this is the repair activity noted in night vision degradation in experiments with lifeguards. For damage above the night vision degradation threshold, the experiment disclosed that the night vision would gradually improve overnight but that the gains would lag below the level of vision the night before. If adequate protection was given during the day however, the eye's night vision would return to normal after a few weeks as the cell renewal processes caught up.

With longer exposure times, the time available for renewal mechanisms to act become more significant. For solar retinitis, the time scale is short. The rate of damage is sufficiently high to cause a lesion and the continuing exposure would result in blindness in a short time. Night vision degradation, in contrast, requires less irradiation and thus lower damage rates than solar retinitis and is more affected on a day to day basis by the efficacy of repair mechanisms of the eye.

When the rate of damage overall is equal to the rate of renewal overall, a threshold is reached above which damage gradually accumulates resulting in the progressive loss of vision. This damage threshold is used in setting the standards discussed in this disclosure and is the basis for the design of the inventive lens.

Functional impairment of the retina is associated with a threshold for damage for a particular time scale of exposure. The threshold for a retinal lesion is at a higher irradiance or for a longer time scale than for night vision impairment.

This lower irradiance, longer term damage which has been quantitatively demonstrated by researchers, has shown that for a given wavelength, smaller irradiances result in damage if the exposure time is longer and for a given irradiance, longer wavelengths can produce damage if the exposure time is longer. To extrapolate to longer time scales and lower irradiances, the efficiency of renewal mechanisms would become more significant in determining the threshold for functional impairment resulting from exposure to damaging influences such as radiation. It has not been proven that the damage mechanism is the same for short time scales as long ones, and the site of injury has been suggested to shift from the retinal pigment epithelium to the receptor layer for long term damage. However, the basic idea of radiation induced damage due to the formation of impaired renewal mechanisms still holds even in this case as well as an action spectrum similar if not identical to the blue light hazard spectrum. This suggests that for long time scales such as a lifetime, the renewal mechanisms are important determinants of the long term prognosis of blindness or eye health.

Damage from high energy visible (blue and violet) and UV photons is due to the formation of reactive molecules which form when cellular materials are struck by the photons. The repair mechanisms involve transport and conversion of highly reactive molecules to less reactive forms without allowing these molecules to react with the cellular materials. The lysosomal enzyme systems that remove damaged molecules are capable of handling sub-threshold damage rates. However, over the threshold, damaged molecules accumulate resulting in impairment to the functions of the cell as the reactive molecules react with the cellular materials and enzymes. This "threshold dependent" damage would be above and beyond the "normal" accumulation of lipofuscin associated with renewal processes. Therefore it is advisable to stay below the threshold in the interest of limiting long term damage to the retina.

The irradiance relative to the threshold is then the single most important factor determining the safety and related comfort of a sunglass lens. The mathematical analysis below has shown that under some light conditions, a filter without a polarizer is insufficient to stay below the calculated threshold. Accordingly, in the area of a glint image on the retina, the tissues on a local scale are closest to threshold and likely to go over it. In order for a conventional sunglass to be able to reduce the glints to a level where they are below threshold, the lenses would have to be so dark as to be nearly useless for vision. The damage to the retina takes place on a small spatial scale, and thus the threshold crossing effect of the glints is under some conditions the only significant damage to the eye during irradiation with blue blocking lenses.

The intensity of photons in the glint can also contribute to the photochemical damage due to the heating of the retina in the vicinity of the glint. High intensity glints of light in the visual field cause a localized area of the retina to be exposed to far more photons per second than outside the focussed glint area. Even wavelengths which are relatively harmless (longer than 600 nanometers) can, under some circumstances cause damage due to thermal heating of the retina in those areas. Thermal heating potentiates photochemical degradation of the receptor segments in the retinal cells, thus encouraging damage to the rods and cones of the eyes. By removing the heated areas, the blue light which impinges on the retina is thus rendered less harmful. The additional contributory effect of the glint may cause the damage threshold to be passed in a given retinal cell, and photochemical damage would then occur in that location of the glint image. Without the glint, the blue photons may be below threshold damage level and no irreversible damage would occur. Removal of the glints removes the heating and thus the passing of the threshold for damage by the blue light in those areas. This thermochemical potentiation of damage has not been taken into account quantitatively in this analysis.

Removing the glints substantially improves the safety of the sunglass without resorting to the more extreme blue blocking that would be necessary to achieve the same degree of retinal safety. It has been found by researchers and those companies which make blue blocking glasses, that many people are disoriented and even nauseated by blue blocking lenses. The effect was so strong that many companies sought the medical market only, ignoring the majority of sunglass wearers in the U.S.

Blue light exposure has also been shown to affect the levels of thyroxin differently from other wavelengths of light in an animal study and this effect might occur in humans. Furthermore, in other animal studies, the blue light has been shown to block the release of melatonin from the pineal gland better than other wavelengths of light. Thus, wearing blue blocking glasses may result in an increased release of melatonin from the pineal. The ramifications of this melatonin increase may be far reaching since melatonin has been shown to affect other hormonal systems which in turn affect metabolism and sex hormones. It is known that manic-depressives' melatonin levels are hyper-sensitive to light levels. Additionally, some people have "winter depression" during the dark short days of winter which was then relieved by exposure to high intensity blue-rich fluorescent lights. Melatonin is also known to increase retinal degeneration under high light illumination.

Researchers generally agree that humans are genetically adapted to a forest cover environment and thus would normally get less blue light exposure and thus more melatonin. Hence wearing the inventive lenses may return melatonin levels to a higher and more historically normal and more healthful level. While blue blocking to some degree may modify the endocrine systems in animals, it appears likely that they modify them for the better, returning the system to a more healthful, natural and balanced state.

For these reasons, the blue blocking is desirable but should not necessarily be done to excess so long as the retina is well protected. Since the benefits to the retina of blocking blue light are very firmly established, some blue blocking is desirable. The ideal situation exists where the glints are removed, so that the illumination is relatively uniform. Under these conditions, a minimum of blue light can be blocked while still keeping all retinal cells below threshold.

Accordingly, a range of lenses which selectively block from 300 to 450 nanometers and which have a sharp cut-on filter from 450 to 550 nanometers with a polarizer have been selected so that the individual has an appropriate amount of short wavelength blocking for adequate protection under a wide range of light environment conditions.

ANALYSIS DEMONSTRATING THE VALUE OF THE INVENTIVE LENS

An analysis was performed to calculate in absolute terms the intensity of hazardous light reaching the eye under various circumstances with optical filters interposed between the eye and the light source. This analysis considers the effect of polarizers on reducing the intensity of light under different hazardous outdoor light conditions. The hazards were compared with known exposure levels for solar retinitis and night blindness resulting in absolute standards for sunglass performance. Under some circumstances only the inventive lens were sufficient to meet the standard.

It has been shown that high levels of blue light (400-500 nanometers range) reaching the retina are harmful to visual performance and the health of the eye. In order to determine the hazard under real and pertinent conditions, models of actual light environment conditions were made. Within those environments, two broad categories of hazardous blue light sources were considered: "glints" and "extended sources".

"Glints" consist of essentially specular reflections of the sun. These sources have some degree of polarization due to the nature of reflections. Glints also subtend a small angle of the eye's field of view. The "extended sources" included diffuse reflections of the sun from such high reflectivity surfaces as snow and clouds as well as the blue light of the sky. These sources subtend a large angle in the eye's field of view and expose large areas of the retina to an essentially uniform level of illumination.

CALCULATION OF HAZARD VALUES FOR SPECULAR REFLECTION SOURCES

A glint is a reflected image of the sun as viewed by the observer's eye. The plane of incidence (defined by the incident and reflected ray) is vertical for all reflections studied in this analysis. This is because most commonly encountered reflections of the sun are reflected from horizontal or nearly horizontal surfaces. The size of this image is given by:

$$y_i = (y_{sol}/s_{sol})*(r/2) \quad [1]$$

where:
  $y_i$ = diameter of the image of the sun.
  $y_{sol}$ = diameter of the sun.
  $s_{sol}$ = distance to the sun.
  r = radius of curvature of the reflective surface (r>0→ convex reflector)

The distance the image of the sun lies behind the convex reflector is given by:

$$s_i = -1/(2/r + 1/s_{sol}) \quad [2]$$

where:
  $s_i$ = The distance the image of the sun lies behind the convex reflector.
  $s_{sol}$ = distance to the sun.
  r = radius of curvature of the reflective surface (r>0→ convex reflector)

The total radiance of the image of the sun is given by:

$$L_i = R * L_{sol} * T_{atmosphere}. \quad [3]$$

where:
  $L_i$ = The radiance of the image of the sun.
  R = the combined reflectance of the reflecting surface.
  $T_{atmosphere}$ = the transmission of the Earth's atmosphere.
  $L_{sol}$ = radiance of the sun as viewed from above the Earth's atmosphere.

The preceding analysis does not consider polarization effects. To consider polarization effects, different reflectance coefficients must be used for the two axes of polarization defined by the plane of incidence. The light emanating from the image of the sun is composed of both horizontally polarized light and vertically polarized light. Since we are assuming a vertical plane of incidence, and since sunlight is randomly polarized, the radiance of vertically polarized light and horizontally polarized light are given by:

$$L_{ihorizontal} = L_{iperp} = (L_{sol}/2) * T_{atmosphere} * R_{perp} \quad [4a]$$

$$L_{ivertical} = L_{ipara} = (L_{sol}/2) * T_{atmosphere} * R_{para} \text{ and,} \quad [4b]$$

$$L_{ihorizontal} + L_{ivertical} = L_i \quad [4c]$$

$$(R_{perp} + R_{para})/2 = R \quad [4d]$$

where:
  $L_{ivertical}$ = the radiance of vertically polarized light radiating from the image of the sun in Watts/(cm$^2$·steradian)
  $L_{ihorizontal}$ = the radiance of horizontally polarized light radiating from the image of the sun in Watts/(cm$^2$·steradian)
  $R_{perp}$ = the reflectance coefficient for light which is polarized perpendicular to the plane of incidence (horizontally polarized light)
  $R_{para}$ = the reflectance coefficient for light which is polarized parallel to the plane of incidence (vertically polarized light)

The factor of 2 enters in because half of the incident sunlight is horizontally polarized and half is vertically polarized.

The reflectance coefficients for reflection of light off of a dielectric material (such as glass or water) are given by:

$$R_{perp} = [\sin(q_i - q_t)/\sin(q_i + q_t)]^2 \quad [5a]$$

$$R_{para} = [\tan(q_i - q_t)/\tan(q_i + q_t)]^2 \quad [5b]$$

$$q_t = (n_i/n_t) * q_i \quad [5c]$$

where:
- $q_i$ = the angle of incidence measured relative to the normal of the plane.
- $q_t$ = the angle of transmittance of the light into the dielectric medium.
- $n_i$ = index of refraction of incident medium (air)
- $n_t$ = index of refraction of transmitted medium (glass, water, etc)
- $R_{para}$ = Reflectance coefficient for light polarized parallel to the plane of incidence (vertically polarized light). $R_{para}$ = (Intensity of reflected light which is polarized parallel to plane of incidence)/(Intensity of incident light which is polarized parallel to plane of incidence)
- Rperp = Reflectance coefficient for light polarized perpendicular to the plane of incidence (horizontally polarized light). Rperp = (Intensity of reflected light which is polarized perpendicular to plane of incidence)/(Intensity of incident light which is polarized perpendicular to plane of incidence)

The angle subtended by the image of the sun as viewed by the observer's eye is given by:

$$a_e = A\tan(y_i/(s_e+s_i)) \qquad [6]$$

where:
- $a_e$ = The angle subtended by the image of the sun as viewed by the observer's eye.
- $y_i$ = diameter of the image of the sun.
- $s_e$ = distance between observer's eye and reflecting surface.
- $s_i$ = distance image is behind reflecting surface.

The corneal irradiance caused by the image of the sun is given by:

$$E = \text{pi}*L_i*(\sin(q_e))^2 \qquad [7]$$

where:
- E = corneal irradiance caused by image of the sun
- $L_i$ = radiance of the image of the sun
- $q_e = a_e/2$ = half angle subtended by the image of the sun as viewed by the observer's eye.

The different reflection coefficients for the two axes of polarized light lead to separate radiances and irradiances for each axes of polarization. The irradiances for the horizontal and vertically polarized light are given by:

$$E_{horizontal} = \text{pi}*L_{ihorizontal}*(\sin(q_e))^2 \qquad [8a]$$

$$E_{vertical} = \text{pi}*L_{ivertical}*(\sin(q_e))^2 \qquad [8b]$$

where:
- $E_{horizontal}$ = the corneal irradiance of horizontally polarized light caused by the image of the sun.
- $E_{vertical}$ = the corneal irradiance of vertically polarized light caused by the image of the sun.

The different reflection coefficients for the two axes of polarized light lead to separate radiances and irradiances for each axis of polarization. The reflectance coefficients shown above indicate that the light which is polarized perpendicular to the plane of incidence is reflected more strongly. Consequently, polarized sunglass lenses are oriented so that they block the light which is polarized perpendicular to the plane of incidence. Since the polarizers used are aligned so that they block virtually all of the light which is polarized perpendicular to the plane of incidence, the total corneal irradiance after the light from the image of the glint has passed through the polarizer is given by:

$$E_p = E_{vertical} = \text{pi}*L_{ivertical}*(\sin(q_e))^2 = \text{pi}*(L_{sol}/2)*T_{atmosphere}*R_{para}*(\sin(q_e))^2 \qquad [9]$$

The standards concerning exposure to hazardous levels of blue light are expressed in terms of hazard-weighted irradiance or hazard-weighted radiance. This hazard function incorporates the fact that certain wavelengths of light are more damaging to the retina than others. In general, the shorter the wavelength of light the more damaging it is. This is due to the photochemical nature of the actinic damage mechanism. However, the ultraviolet (UV) wavelengths of light are largely absorbed by the cornea, lens, and aqueous and vitreous humors of the eye and therefore very little of the short wavelength UV light reaches the retina. These two effects combine to produce a retina hazard function which peaks in the blue region of the spectrum at about 450 nm. The equations for calculating the hazard weighted radiances and irradiances are given by:

For extended sources:

$$L_b = \sum_{400 \text{ nm}}^{1400 \text{ nm}} L_{source}(l)*BLH(l)*\Delta l \quad \text{for } t > 10000 \text{ seconds} \qquad [10]$$

where:
- $L_b$ = the hazard weighted radiance in $W/(cm^2*sr)$
- $L_{source}(l)$ = the spectral radiance of the source as a function of wavelength in $W/(cm^2*sr*nm)$
- BLH(l) = the blue light hazard function as a function of wavelength
- $\Delta l$ = the interval of wavelength at which measurements are taken and the calculation is made. In this study spectral data was taken at intervals of 5 nm.

And for point sources subtending less than 11 millirad (approximately 0.62 deg.) we have:

$$E_b = \sum_{400 \text{ nm}}^{1400 \text{ nm}} E_{source}(l)*BLH(l)*\Delta l \quad \text{for } t > 10000 \text{ seconds} \qquad [11]$$

where:
- $E_b$ = the hazard weighted irradiance in $W/cm^2$
- $E_{source}(l)$ = the spectral irradiance of the source as a function of wavelength in $W/(cm^2*nm)$
- BLH(l) = the blue light hazard function as a function of wavelength
- $\Delta l$ = the interval of wavelength at which measurements are taken and the calculation is made. In this study spectral data was taken at intervals of 5 nm.

The standards given for the two types of hazardous sources are given by researchers in the field as follows:

$$L_b < = 0.01 W/(cm^2*sr) \text{ for } t > = 10^4 \text{ seconds} \qquad [12]$$

$$E_b < = 1 \text{ microwatt/cm}^2 \text{ for } t > = 10^4 \text{ seconds} \qquad [13]$$

To calculate the effect of a spectrally selective filter on the hazard weighted irradiance and radiance of a hazardous source, the spectrum of the source as viewed through the selective filter must be calculated as follows:

$$L_{filterdsource}(l) = T_{filter} \cdot L_{source}(l) \text{ and,} \quad [14]$$

$$E_{filteredsource}(l) = T_{filter} \cdot E_{source}(l) \quad [15]$$

The blue light hazard of the source when viewed through the filter can now be calculated by inserting $L_{filteredsource}(l)$ in place of $L_{source}(l)$ in eqn [10] and inserting $E_{filteredsource}(l)$ in place of $E_{source}(l)$ in eqn [11].

Finally the blue light hazard of a glint as viewed through the combination of a spectrally selective filter and a properly oriented polarizer is calculated by substituting $L_{ivertical}$ in place of $L_{source}$ in eqn [14] and substituting $E_{ivertical}$ in place of $E_{source}$ in eqn [15] and proceeding with the calculation by inserting the resulting source radiance and irradiance in eqns [10] and [11] respectively.

In this analysis these extended sources are assumed to have a negligible degree of polarization. Blue skylight is horizontally polarized to some degree in the direction opposite the position of the sun but most extended sources do not polarize light appreciably.

The quantity of importance for extended source optical hazards is the radiance, $L_d$. For extended sources such as the blue sky, the radiance is measured directly and weighted by the procedure described by eqn[11] to produce the blue light hazard weighted radiance. For extended sources illuminated by the sun which are essentially white lambertian scatterers such as fresh snow, dry white sand, or the top of a cloud deck the radiance is given by:

$$L_d = R_d \cdot L_{sol} \cdot (\sin(q_{sol}))^2 \quad [16]$$

The blue light hazard weighted radiance of solar illuminated extended sources is given by:

$$L_{db} = R_d \cdot L_{solb} \cdot (\sin(q_{sol}))^2 \quad [17]$$

where:
$L_{db}$ = the blue light hazard weighted radiance of the extended scattering source which is illuminated by the sun.
$R_d$ = the diffuse reflectance coefficient of the scattering surface.
$q_{sol}$ = the half angle subtended by the sun.
$L_{solb}$ = the blue light hazard weighted radiance of the sun as calculated below:

$$L_{solb} = \sum_{400 \text{ nm}}^{1400 \text{ nm}} L_{sol}(l) \cdot BLH(l) \cdot \Delta l \quad [10]$$

$$\text{400 nm for } t > 10000 \text{ seconds}$$

where:
$L_{solb}$ = the hazard weighted radiance of the sun in W/(cm$^2$·sr)
$L_{sol}(l)$ = the spectral radiance of the sun as a function of wavelength in W/(cm$^2$·sr·nm)
BLH(l) = the blue light hazard function as a function of wavelength
$\Delta l$ = the interval of wavelength at which measurements are taken and the calculation is made. In this study spectral data was taken at intervals of 5 nm.

DERIVATION OF METHOD FOR QUANTITATIVELY SELECTING CUT-ON WAVELENGTHS:

Equations [11] and [13] can be combined to give:

$$1 \text{ microwatt/cm}^2 \geq E_b = \sum_{400 \text{ nm}}^{1400 \text{ nm}} E_{source}(l) \cdot BLH(l) \cdot \Delta l \quad [18]$$
(or 0.02 microwatt/cm$^2$)

where:
$E_b$ = the hazard weighted irradiance in W/cm$^2$
$E_{source}(l)$ = the spectral irradiance of the source as a function of wavelength in W/(cm$^2$·nm)
BLH(l) = the blue light hazard function as a function of wavelength
$\Delta l$ = the interval of wavelength at which measurements are taken and the calculation is made.

The corneal irradiance which results after the incident light has passed through the spectral filter = $E_{bfiltered}$. By substituting $E_{filteredsource}(l)$ for $E_{source}(l)$ and $E_{bfiltered}$ for $E_b$ in equation [18] we have the following equation for $E_{bfiltered}$:

$$1 \text{ microwatt/cm}^2 \geq E_{bfiltered} = \sum_{400 \text{ nm}}^{1400 \text{ nm}} E_{filteredsource}(l) \cdot BLH(l) \cdot \Delta l \quad [19]$$
(or 0.02 microwatt/cm$^2$)

where:
$E_{filteredsource}(l)$ = the spectral irradiance of the source after it has passed through the spectrally selective filter.
$E_{bfiltered}$ = the hazard weighted irradiance of the source after it has passed through the spectrally selective filter.

Substituting equation [15] into [19] yields:

$$1 \text{ microwatt/cm}^2 \geq E_{bfiltered} = \sum_{400 \text{ nm}}^{1400 \text{ nm}} T_{filter}(l) \cdot E_{source}(l) \cdot BLH(l) \cdot \Delta l \quad [20]$$
(or 0.02 microwatt/cm$^2$)

where: $T_{filter}(l)$ = the spectral transmission of the sunglass filter without polarization.

Since the polarizers used are aligned so that they block virtually all of the light which is polarized perpendicular to the plane of incidence, the total corneal irradiance after the light from the image of the glint has passed through the polarizer is given by:

$$E_p = E_{vertical} \quad [9]$$

Therefore, only $E_{vertical}(l)$, the vertical component of $E_{source}(l)$, reaches the cornea. Thus the total corneal irradiance, in Watts/cm$^2$, which results after the incident light has passed through the spectrally selective filter and the polarizer is defined as $E_{bpolfiltered}$ and is given by:

$$1 \text{ microwatt/cm}^2 \geq E_{bpolfiltered} = \quad [21]$$
(or 0.02 microwatt/cm$^2$)

-continued $$\sum_{400 \text{ nm}}^{1400 \text{ nm}} T_{filter}(l) * E_{vertical}(l) * BLH(l) * \Delta l$$

where: $E_{vertical}(l)$ = the unfiltered corneal spectral irradiance of vertically polarized light caused by an image of the sun in W/(cm$^2$*nm).

To choose the cut-on wavelength which is appropriate for the environmental conditions, typical values of $E_{vertical}(l)$, the vertically polarized component of the unfiltered corneal irradiance, must be measured. Equation [22] may now be solved iteratively for the cut-on wavelength, $I_{cut-on\ wavelength}$, which results in a spectrum which reduces the corneal irradiance to a safe value (< =1 microwatt/cm$^2$ for solar retinitis, < =0.02 microwatt/cm$^2$ for night vision loss).

$$1 \text{ microwatt/cm}^2 >= E_{bpolfiltered} = \qquad [22]$$
(or 0.02 microwatt/cm$^2$)

$$\sum_{I_{cut-on\ wavelength}}^{1400 \text{ nm}} T_{filter}(l) * E_{vertical}(l) * BLH(l) * \Delta l$$

where:

$E_{bpolfiltered}$ = the total corneal irradiance, in Watts/cm$^2$, which results after the incident light has passed through the spectrally selective filter and the polarizer.

$E_{vertical}(l)$ = the unfiltered corneal spectral irradiance of vertically polarized light caused by an image of the sun in W/(cm$^2$*nm).

$T_{filter}(l)$ = the spectral transmission of the sunglass filter without polarization.

$BLH(l)$ = the blue light hazard function as a function of wavelength $\Delta l$ = the interval of wavelength at which measurements are taken and the calculation is made.

$I_{cut-on\ wavelength}$ = the cut-on wavelength best suited to the usage environment described by $E_{vertical}(l)$.

A similar argument can be made for extended sources. This derivation uses equations [10], [12], and [14] instead of equations [11], [13], and [15]. This argument yields the following equation which can be solved iteratively for the cut-on wavelength, $I_{cut-on\ wavelength}$, which reduces the radiance viewed by the eye of the sunglass wearer to a safe level (10 mWatt/(cm$^2$*sr) for solar retinitis, 0.2 mWatt/(cm$^2$*sr) for night vision loss):

$$10 \text{ mWatt/(cm}^2*sr) >= L_{bpolfiltered} = \qquad [23]$$
(or 0.02 mWatt/(cm$^2$*sr))

$$\sum_{I_{cut-on\ wavelength}}^{1400 \text{ nm}} T_{filter}(l) * L_{vertical}(l) * BLH(l) * \Delta l$$

where:

$L_{bpolfiltered}$ = the total corneal radiance, in Watt/(cm$^2$*sr), which results after the incident light has passed through the spectrally selective filter and the polarizer.

$L_{vertical}(l)$ = the unfiltered corneal spectral radiance of vertically polarized light caused by an image of the sun in Watt/(cm$^2$*sr*nm).

$T_{filter}(l)$ = the spectral transmission of the sunglass filter without polarization.

$BLH(l)$ = the blue light hazard function as a function of wavelength $\Delta l$ = the interval of wavelength at which measurements are taken and the calculation is made.

$I_{cut-on\ wavelength}$ = the cut-on wavelength best suited to the usage environment described by $L_{vertical}(l)$.

Standards Based On Effects

There have been several research reports presented which describe the microanatomical and functional effects of exposure to certain wavelengths of light. One of these reports found that the 35 to 50 percent transmission of conventional sunglasses was unable to provide protection lasting longer than a day or so while 10 to 12 percent transmission sunglasses are adequate to protect night vision for longer periods. It has also been argued that short wavelength visible light is the effective part of the spectrum in their observed degradation of night vision. From this premise, and by using the original calculations shown above, we are able to calculate the hazard weighted radiance the subjects were exposed to and thus determine the threshold for night vision protection. It appears that the threshold for night vision degradation is at approximately 0.2 mWatt/(cm$^2$*sr). The threshold for solar retinitis is 10 mWatt/(cm$^2$*sr).

Some retinal irradiance studies have been in terms of exposure to extended sources while others are in terms of specular sources. The image of a specular source is not perfectly focussed and is moved across the retina by the motion of the eye resulting in a larger effective area and lower effective irradiance than would be expected if the irradiance were perfectly focussed in one place. A 1 microWatt/cm$^2$ point source produces the same retinal irradiance as a 10 milliwatt/cm$^2$*sr extended source over the area it affects. The resulting damage thresholds are shown in the Table below:

| | Thresholds for Damage | |
|---|---|---|
| Damage | Specular | Extended |
| Solar Retinitis | 1.0 microW/cm$^2$ | 10.0 mW/(cm$^2$*sr) |
| Night Vision Loss | 0.02 microW/cm$^2$ | 0.2 mW/(cm$^2$*sr) |

For our purposes in developing a quantitative method of choosing the appropriate cut-on wavelength, the more protective standard of 0.02 microW/cm$^2$ (for point sources) and 0.2 mW/(cm$^2$*sr) (for extended sources) was chosen. However, for applications where preservation of night vision is not important, the less protective standard of 1.0 micro W/cm$^2$ (for point sources) and 10.0 mW/(cm$^2$*sr) (for extended sources) can be used.

Standards based on the above Table are presently not used in the sunglass industry and are an innovation of the inventors. The standard is referred to as the Eye Protection Factor (EPF). The EPF standard is based on how well the sunglass blocks harmful radiation relative to the thresholds described above for a standard condition and results in a rating number which a consumer can use in a manner similar to the Sun Protection Factor (SPF) numbers shown on suntan lotions.

In view of the above disclosure it is the primary object of the invention to disclose a sunglass lens design and process for making the lens that uses a combination dye and a polarizer to produce a lens that substantially blocks ultraviolet radiation, blue light, and horizontally polarized light. The result of this is a lens that:
 can be used for an extended period of time without damage or discomfort,
 improves visual acuity,
 protects against long term eye damage,
 preserves night vision,
 reduces risk of eye disease,
 reduces the onslaught of radiation which results in aging of the eye tissues and taxes regenerative processes in the eye.

In addition to the primary objects it is also an object of the invention to have a lens that is:
 cost effective and safe to own,
 cost effective and safe to manufacture,
 mechanically easy to handle and use,
 adaptable to a variety of sunglass frames,
 adaptable to a variety of visual environments.
 can be used in applications other than for sunglasses These and other objects and advantages of the invention will become apparent from the subsequent detailed description of the invention and the claims taken in conjunction with the accompanying drawings.

BEST MODE FOR CARRYING OUT THE INVENTION

The best mode for carrying out the inventive Ultraviolet radiation and blue light blocking polarized lens 10 is presented in terms of a preferred embodiment that is primarily designed for mounting on a pair of sunglasses. The lens 10 substantially blocks horizontally polarized light and selectively blocks wavelengths in the electromagnetic spectrum that lie between 300 and 549 nanometers and allows 30 to 40 percent of wavelengths in the visible portion of the spectrum, that are longer than 625 nanometers, to be transmitted. The selective blocking is controlled by a sharp cut-on filter selected to cut-on at either 450, 500, 515, 530, or 550 nanometers. Only wavelengths longer than 300 nanometers need be blocked due to atmospheric absorption of shorter wavelengths.

The lens 10 in the disclosure that follows refers to various terms. To facilitate the understanding of the invention, these terms are initially defined.

Electromagnetic spectrum. For the purpose of this invention, the spectrum has a lower limit of 300 nanometers and an upper limit of 780 nanometers. The visible portion of the spectrum is further defined as falling between 400 and 780 nanometers.

Transmission. The percentage of light that is passed through a lens.

Blocking. The opposite of transmission and is a measure of the percentage of light that is either reflected by the surface or surface coatings or absorbed by the dye or plastic of the lens.

Substantially blocking. When used with reference to wavelengths, it is defined as blocking over 99 percent of the incident radiation at each and every wavelength. When used with reference to polarization, it is defined as blocking 80 percent or more of the horizontally polarized incident radiation at each and every wavelength. Conversely, substantially transmitting, when used with reference to wavelengths, is defined as transmitting more than 1 percent of the incident radiation at each and every wavelength. When substantially transmitting is used with reference to polarization it is defined as transmitting 20 percent or more of the horizontally polarized incident radiation at each and every wavelength.

Sharp cut-on. For the purpose of this invention, sharp cut-on is defined in the context of a dye or filter, having a cut-on slope that rises more than one half percent (0.5%) change in transmission for every one nanometer of increasing wavelength change. The cut-on slope is that portion of the transmission spectra of a cut-on dye that represents the transition between substantially blocking region and the substantially transmissive region. A cut-on filter is an optical filter that substantially blocks all wavelengths shorter than the cut-on wavelength and substantially transmits all wavelengths that are longer than the cut-on wavelength. The cut-on wavelength is that wavelength in the transition zone at which the transmission is 1 percent.

Combination dye. For the purpose of this invention, a combination dye is defined as being made from a mixture of two dyes who's ultraviolet transmission holes do not substantially overlap.

The preferred embodiment of the invention, as shown in FIGS. 1 through 8, is comprised of the following seven major elements: a plastic lens 12, a sharp cut-on filter 14, a horizontally polarizing film 16, a combination dye 18, a dispersed orange three sharp-cut-on dye 20, a dispersed red two sharp-cut-on dye, and a dispersed yellow twenty-three sharp-cut-on dye 24.

The lens 10 as used in this invention is primarily a blocking lens rather than a transmissive lens and is cast from an optical plastic or optical glass. In the preferred embodiment, the lens is cast from an optical hard-resin plastic made from a di-allyl glycol carbonate monomer such as a. CR-39 polymer. CR-39 is a registered trademark of the Pittsburgh Plate Glass Company having its principal offices in the United States of America. The CR-39 polymer possesses properties that under controlled conditions allows the lens to be easily dyed with the selected dispersed dyes, described infra, that provide the required wavelength blocking.

Sunlight is composed primarily of visible light and invisible radiations known as Ultraviolet and Infrared. Most persons exposed to bright light, especially sunlight, for any period of time are more comfortable when wearing sunglasses that block wavelengths in the 400 to 780 nanometer range. Conventional sunglass lenses that block in this range reduce excessive glare, which can cause eye discomfort but they hamper visual acuity because of their necessarily low transmission.

The blocking feature of the inventive lens 10 is achieved by the sharp cut-on filter 14 which is used in combination with the horizontally polarizing film 16. The function of the filter 14 is best understood by referring to FIG. 1 which discloses the spectral curves of the invention.

The spectral curves are divided into a blocking zone, a transition zone and a transmissive zone. The curves define the transmission spectra of a family of sunglass lenses having sharp cut-on filters at wavelengths of 450, 500, 515, 530, and 550 nanometers.

If a filter 14 having a cut-on at 450 nanometers is selected, the blocking zone and the transmissive zone are common to other members of the family. In this case, wavelengths between 300 and 449 nanometers are substantially blocked up to the transition zone where the sharp cut-on filter 14 cuts-on at 450 nanometers and steeply rises up to the transmissive zone where 30 to 40 percent of the wavelengths that are longer than 625 nanometers are transmitted.

If a cut-on filter 14 other than at 450 nanometers is selected, the range of the blocking zone increases (displaced horizontally). For example, if a 500 nanometers cut-on filter is selected, wavelengths between 300 and 499 nanometers would be blocked up to and into the transition zone where the sharp cut-on filter 14 would cut-on at 500 nanometers; likewise, a cut-on at the maximum 550 nanometer would allow wavelengths between 300 and 549 nanometers to be blocked before the cut-on filter cuts-on at 550 nanometers. In all cases of the preferred embodiment, the transmissive zone, beyond 625 nanometers, remains fully open transmitting between 30 to 40 percent at each and every wavelength out into the infrared region. In the preferred embodiment, 30 to 40 percent of wavelengths longer than 625 nanometers, are transmitted. However, the transmittance of the transmissive zone beyond the 625 nanometer point can be increased to any range between 10 and 90 percent by the proper selection of the combination dye 18 and the polarizing film 16.

The principal novelty of the invention is in the ability of the lens 10 by means of the sharp cut-on filter 14 in combination with the polarizer 16 to block ultraviolet radiation, blue light and horizontally polarized light. While a calming effect is achieved by wearing only blue blocking lenses, the inclusion of the polarizer 16 substantially increases the calming effect and substantially improves vision without visual discomfort. Additionally, the inventive lens allows a specific degree of safety without affecting the hormonal balance of the body any more than necessary. These surprising and unexpected results have been explained by way of a hypothesis after the combination was reduced to practice and the effects were experienced first hand. The complete explanation of some effects must await further understanding of the human brain and the interaction of the human eye with light. In contrast, the limited improvement in visual acuity and eye protection afforded by the elimination of the Ultraviolet radiation and the reduction of blue light content is well recognized by researchers in the field.

The process that resulted in a successful reduction to practice of the innovative lens 10 was not obvious at the outset. The economic production of UV and blue blocking polarizing sunglasses is hampered by the fact that the currently manufactured plastic lens polarizers generally consist of a sheet of heat sensitive polarizing film laminated between two layers of the CR-39 polymer lens. The polarizer is formed by stretching the thin film so that the film molecules are aligned in a way that light passing through the lens is polarized. When this film is laminated in the cast CR-39 polymer it can withstand the heating that is normally used to hot-dip dye lenses with cosmetic tints. These tints are usually very light shades of pastel colors that add a decorative and individualizing feature to the lens. The requirement for dying the lens to the level that is required by the instant invention for full eye protection and maximum visual acuity required a time and temperature in the hot-dip dye vessels that destroyed the polarizing effect of the lens 10.

Figure 2:
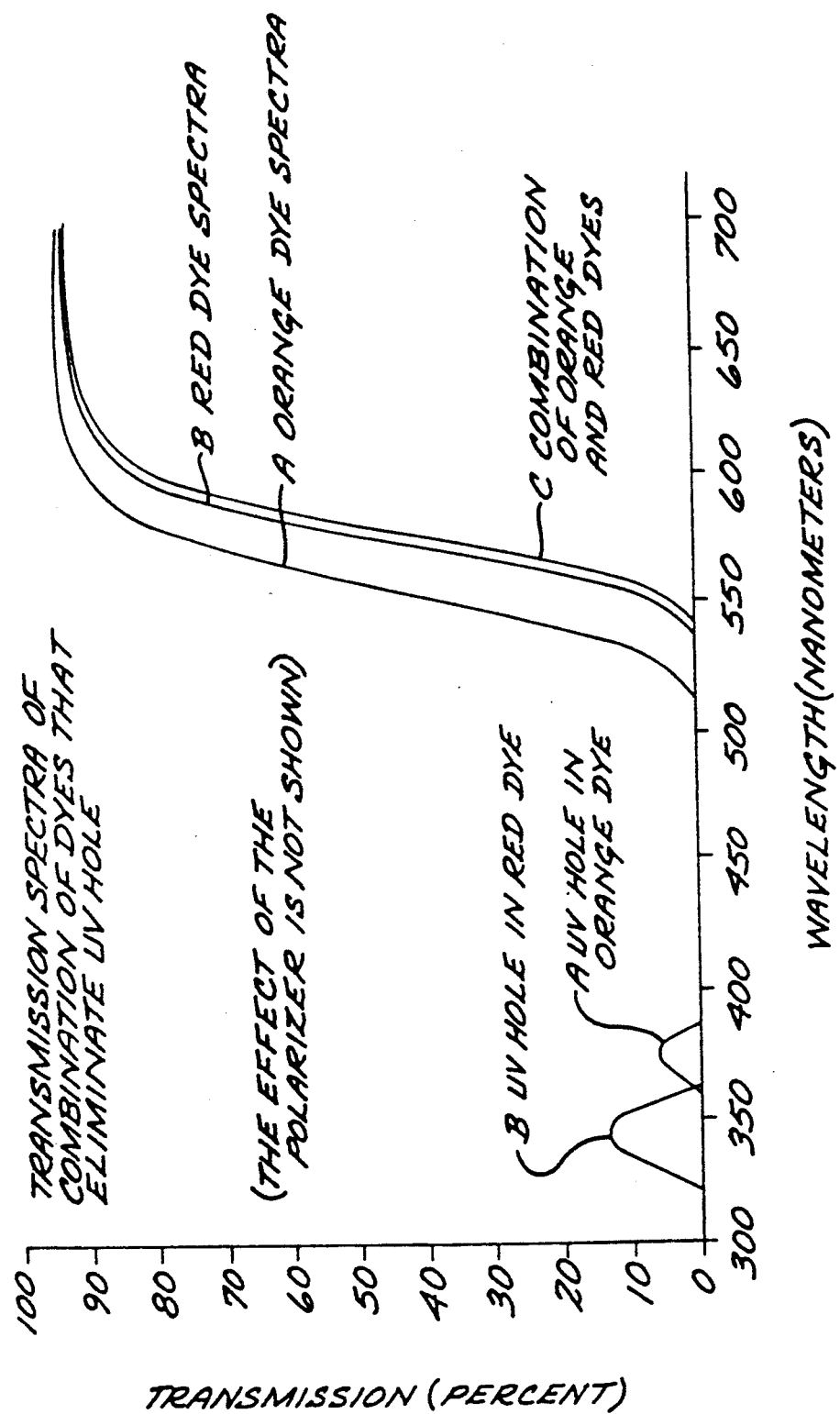
FIG. 2 is a graph that shows the transmission spectra of a combination of dyes that eliminate ultraviolet holes.

It is also known in the art that commercially available dispersed sharp cut-on dyes suitable for the hot-dip dying of CR-39 plastic lenses have a significant UV radiation transmission. This UV transmission is sometimes referred to as a "UV hole". The cut-on dyes, as shown in FIG. 2, Curves A and B, used in this invention each have a "UV hole". If the lens 12 is allowed to become sufficiently dark by extending the dye time, the UV hole will be absorbed to less than one percent. Unfortunately, the time required for this UV reduction will cause the polarizer to fall due to the time the polarizing film 16 is heated in the dye and exposed to the dye chemicals.

The minimum time the lens 12 must be in the dye is determined by how long it takes to fill the UV hole. By using the combination dye 18, as shown in FIG. 2 Curve C, the time and temperature required to remove the UV holes can be reduced as shown in FIG. 2 curve A to allow the polarizer film 16 to survive the manufacturing process.

The hot-dip dyeing process is the most commonly used process for dying ophthalmic lenses and is the basis for the best mode process. The dyes that are used are dispersed dyes, that is, they are molecules of oil soluble dye encased in a surfactant skin. The dyes are dispersed in water at a temperature of 98±1 degree centigrade. When an encased molecule of dye contacts the plastic surface the surfactant skin breaks and the oil soluble dye molecule diffuses into the surface of the plastic lens. Increasing the dye concentration in the boiling water dispersion does not increase the dyeing rate significantly but the danger that the dispersion will break down increases dramatically. When many dye molecules collide with one another their surfactant skin can break down and they can aggregate into a greasy lump of dye molecules that have lost their surfactant skins. This lump sticks to the lens surface where it will form a visible spot on the lens. If the particular sharp cut-on dispersed dye is allowed to diffuse into the plastic for a long enough time and at a high enough temperature the UV hole will be reduced to acceptable levels to provide adequate eye protection and the required cut-on wavelength.

What was not known to the ophthalmic lens dying industry was the fact that some dyes have their UV holes at slightly different wavelengths from one another. This off-set of the UV holes in different dyes is the discovery that induced the process part of the instant invention.

The instant invention makes the sharp cut-on dyeing of heat sensitive polarizers technically and economically feasible. In the Best Mode Table, as shown in FIG. 3, it can be observed that a combination of a dispersed yellow twenty-three dye 24 and a dispersed orange three dye 20 will produce the desired results of a sharp cut-on filter in the shorter (light orange) wavelengths; and a combination of a dispersed orange three dye 20 with a dispersed red two dye will produce a sharp cut-on filter with longer (dark orange) wavelengths. The dye concentrations were empirically determined to produce a combination of dyes that would not produce the greasy lumps and would dye the heat sensitive polarizer lens fast enough that they would not be destroyed. The best mode table of FIG. 3 provides the dye combination 18, the required time and temperature to provide the specific cut-on wavelength desired. The table also includes the recommended uses for the UV and blue blocking polarizing lens 10. Although not considered a preferred method, the lens may be applied by the combination dye at a temperature of 37±1 degree centigrade where the time is between 7 and 10 days.

Figure 4:
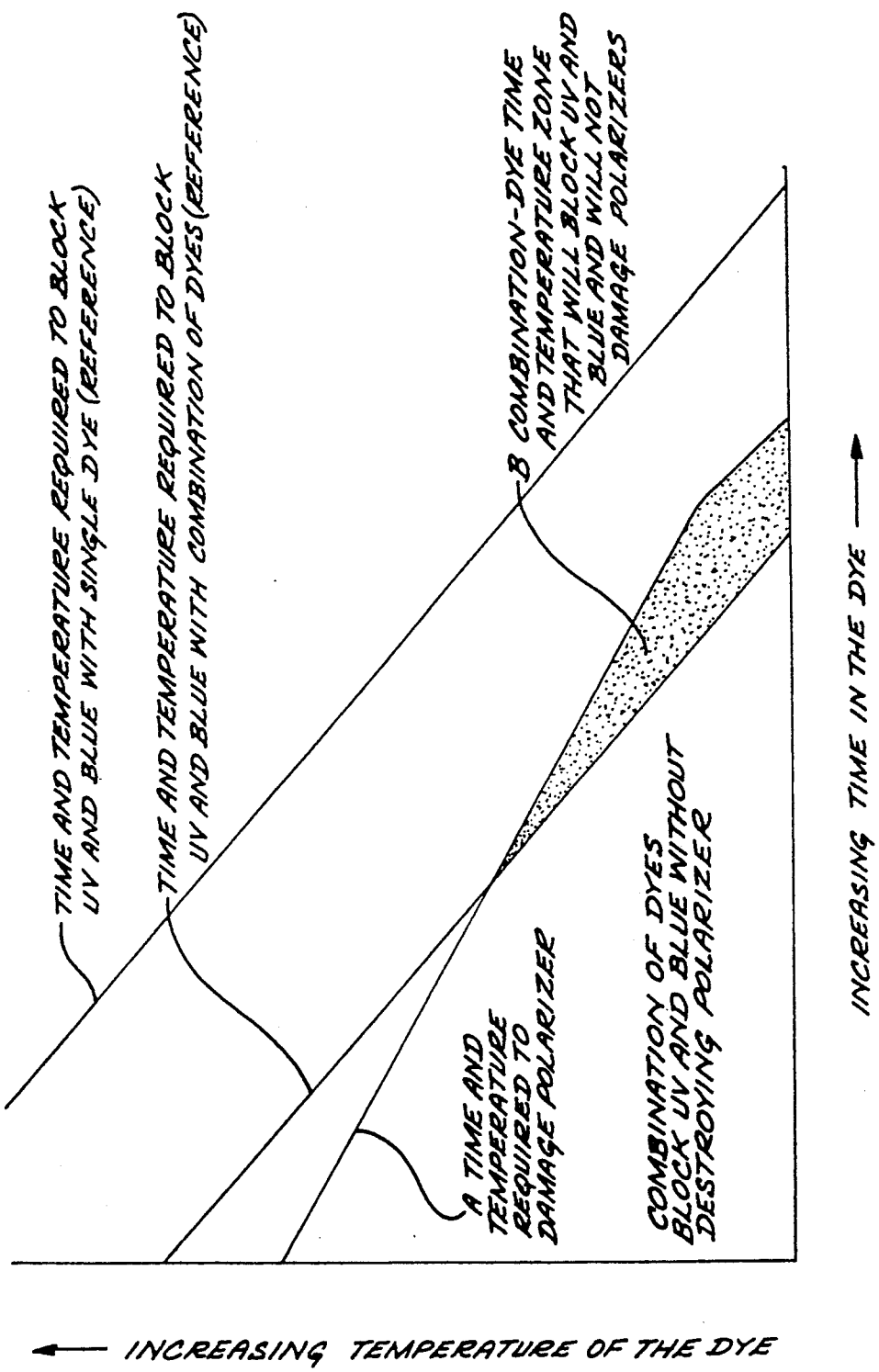
FIG. 4 is a graph that shows the failure curve of polarizers and the preferred area where a polarizer can be safely processed with the combination hot-dip dyes.

The polarizer 16 combined with the lens 12 adds a polarizing screen that blocks horizontally polarized light. The film used, as previously mentioned, is sensitive to chemical and temperature damage. Thus a polarized film that is exposed to heat and chemicals (such as a dye) after a period of time will fail and cease to block the polarized light. A typical polarizing film 16 failure curve is shown in FIG. 4 Curve A. The area above Curve A constitutes the polarizer failure region while below Curve A is the safe region. Therefore, to safely dye polarizing lenses, the dyes must be selected so that the required optical density can be achieved within the enclosed area shown in FIG. 4 area B which is below the polarizer failure Curve A. In other words, the dye time and temperatures shown in FIG. 3 must be selected to fall within the safe region shown in area B. The downward inflection of Curve A is due to the chemical degradation of the polarizing lens that occurs after extended periods of time in the dye at low temperature.

A search was made for sources of polarizers which had as high a Curve A as possible. One such lens, a heat resistant polarizer which did not delaminate or fail at required time and temperature, is known as "R-plano smoke color as in invoice 10-324" and is procured from the Alpha Company Ltd. in Japan. Of the numerous sources examined, an exceptionally heat resistant lens manufactured by the Polarlite Co. in Seattle, Wa., was also found that could sometimes be dyed with a single dye (orange or yellow) for longer times and higher temperatures. However, because of the expensive heat resistant lens, the use of one dye is not considered the best mode, but it is another possible way to make the lens 10.

Other ways to make the polarized lens include:
   laminating a film onto or between a pre-dyed UV and blue blocking lens blank,
   dying the lens with an embedded polarizer in a solvent dye, and/or mixing the dye into the monomer before molding around a polarizing film.

While under some circumstances these techniques could be desirable, their complexity, tooling costs and minimum manufacturing quantities make them economically unfeasible for smaller scale operations.

For intermediate scale production, lenses can be dyed using the best mode time, temperatures and dye concentrations shown in FIG. 3.

For large scale production, lenses can be dyed using the best mode time, temperatures and dye concentrations in FIG. 3.

After the lenses are dyed they are edged by standard industrial edging machines well known in the ophthalmic industry. The lenses are then mounted in metal or plastic frames suitable for the various occupations and recreations mentioned in the Best Mode Table of FIG. 3. Before the completed sunglasses are shipped they are compared to spectral standards to insure they meet the required cut-on filter requirements and the required polarization performance. The sunglasses are inspected for imperfections and proper assembly in the frames.

The polarizing film 16 as used with various combinations of dye locations is shown in crossection in FIGS. 5, 6, and 7.

In FIG. 5, the dye is absorbed into the surface of the plastic lens 12 and the polarizing film 16 is laminated between two lens halves of cast or preformed plastic. The dye in this case is absorbed into the lens surface by a hot-dip dispersed dye process or a cold-dip solvent dye process.

In FIG. 6, the dye is mixed into the cast or preformed plastic lens 12 before the plastic is cast. Two halves are then laminated on either side of the polarizing film.

In FIG. 7, the polarizing film 16 is laminated and the dye is in a coating or a laminated dyeable film that is bonded to the inside or outside of a plastic or glass lens 12. If the plastic or glass lens is photochromic and the dyeable film is on the inside (concave) of the lens the dyes will block the UV necessary to activate the photochromic material before the UV enters the eye.

The synergistic effect of having a lens 12 with a polarizer 16 and a combination dye 18 that substantially absorbs blue light results in a lens that provides effective protection to the retina. The ideal situation is to minimize the need for blue blocking, by staying below the damage-repair threshold, and eliminating the thermal heating of the retina by the glints of light that pass across the retina as discussed in the Disclosure of the Invention section. The inventive lens 10 accomplishes this protection by blocking the horizontally polarized glints of light in the blue and UV wavelengths.

The combination dye 18 available for use with the lens 12 can be selected to substantially block all wavelengths in the electromagnetic spectrum between 300 and 549 nanometers. The specific cut-on wavelength selected within this spectral range is dependent upon the comfort of the user in a specific usage environment. The specific cut-on of the lens depends upon the time, temperature, and component dyes used to make the combination dye.

To process a lens 12, an optical plastic lens having a polarizing film 16 embedded therein is procured. If a cut-on wavelength at 450 nanometers is desired, a combination dye 18 is applied to lens 12 by a hot-dip combination dispersed dye process. The process essentially consists of immersing the lens into a vessel containing a mixture of dispersed yellow twenty-three dye 24 and a dispersed orange three dye 20 in a concentration ratio of approximately 1 to 1. The lens 12 remains in the vessel for a period of 2.5 minutes at a temperature of 98±1 degree centigrade.

If a cut-on wavelength at 500 nanometers is desired, the lens 12 is immersed into a vessel containing a mixture of dispersed yellow twenty-three dye 24 and a dispersed orange three dye 20 in a concentration ratio of approximately 1 to 1 for a period of 5.0 minutes at a temperature of 98±1 degrees centigrade.

For a cut-on wavelength at 515 nanometers, the lens 12 is immersed into a vessel containing a mixture of dispersed yellow twenty-three dye 24 and a dispersed orange three dye 20 in a concentration ratio of approximately 1 to 1 for a period of 12.0 minutes at a temperature of 98±1 degrees centigrade.

For a cut-on wavelength at 530 nanometers, the lens 12 is immersed into a vessel containing a mixture of dispersed red two dye and a dispersed orange three dye 20 in a concentration ratio of approximately 1 to 1 for a period of 4.5 minutes at a temperature of 98±1 degrees centigrade.

For a cut-on wavelength at 550 nanometers, the lens 12 is immersed into a vessel containing a mixture of dispersed red two dye and a dispersed orange three dye 20 in a concentration ratio of approximately 1 to 1 for a period of 12.0 minutes at a temperature of 98±1 degrees centigrade.

The best mode process for preparing the lens 12 is the hot-dip combination dispersed dye process described supra. Other processes that may also be used to apply the combination dye 18 or individual dyes include a laminate film process, a solvent dyed coating process, a cold-dip solvent-dye process and a pre-solvent-dyed molded-plastic process. The additional processes are well known in the art and are therefore not described.

The processes that use the combination dye 18 may be used for all the sharp cut-on filters 14 described earlier. For filters that cut-on between 450 and 530 a single orange or red hot-dip dye may be used with special heat resistant polarizing lenses.

In this alternative process, if a cut-on at 450 nanometers is desired, the lens 12 is immersed into a vessel containing the yellow twenty-three dye 24 for a period of 16 minutes at a temperature of 98±1 degrees Centigrade.

For a cut-on at 500 nanometers, the lens 12 is immersed into a vessel containing the orange three dye 20 for a period of 5 minutes at a temperature of 98±1 degrees Centigrade.

For a cut-on at 515 nanometers, the lens 12 is immersed into a vessel containing the orange three dye 20 for a period of 12 minutes at a temperature of 98±1 degrees Centigrade.

For a cut-on at 530 nanometers, the lens 12 is immersed into a vessel containing the orange three dye 20 for a period of 18 minutes at a temperature of 98±1 degrees Centigrade.

For a cut-on at 550 nanometers, the lens 12 is immersed into a vessel containing the red two dye for a period of 18 minutes at a temperature of 98±1 degrees Centigrade.

The standard temperature of 98±1 degree as used in the preferred process may be changed to 37±1 degrees Centigrade. When the lens 12 is immersed at this lower temperature, the time required is about 7 to 10 days.

The combination dye 18 selected for use with the lens 12 is dependent upon its ultimate use. All reasonable viewing problems can be solved by using a polarized lens incorporating sharp cut-on filter 14. Five typical problem situations are considered: a lifeguard, a boater, a fisherman, a driver, and a pilot—the hazard weighted irradiance referred to in the discussion as well as other numerical and technical notations are derived and described in the Disclosure of the Invention section. The spectra of these lenses are shown in FIG. 1.

The typical situation for the lifeguard is as follows: The time is noon, with the sun at zenith. The lifeguard is 8 meters away from the water which has waves on it with a radius of curvature of 3 meters. The hazard weighted irradiance is 3.27 microW/cm$^2$ which is far above the threshold for both solar retinitis and night vision loss. With a 500 cut-on filter, the irradiance drops to 0.036 microW/cm$^2$ which is below the threshold for solar retinitis but above the threshold for night vision loss. With the addition of the polarizer, the hazard weighted irradiance is reduced to 0.004 microW/cm$^2$ which is below the night vision loss threshold.

The typical situation for the boater is as follows: The time is noon, with the sun at zenith. The boater is 4.5 meters away from the water which has waves on it with a radius of curvature of 3 meters. The hazard weighted irradiance is 8.20 microW/cm$^2$ which is far above the threshold for both solar retinitis and night vision loss. With a 515 cut-on filter, the irradiance drops to 0.063 microW/cm$^2$ which is below the threshold for solar retinitis but above the threshold for night vision loss. With the addition of the polarizer, the hazard weighted irradiance is reduced to 0.007 microW/cm$^2$ which is below the night vision loss threshold.

The typical situation for the driver is as follows: The time is noon, with the sun at zenith. The driver is 5 meters away from the glass window of the car in front of it. The glass window has a radius of curvature of 4 meters. The hazard weighted irradiance is 39.60 microW/cm$^2$ which is far above the threshold for both solar retinitis and night vision loss. With a 530 cut-on filter, the irradiance drops to 0.24 microW/cm$^2$ which is slightly above the threshold for solar retinitis and far above the threshold for night vision loss. With the addition of the polarizer, the hazard weighted irradiance is reduced to 0.002 microW/cm$^2$ which is below the night vision loss threshold.

The typical situation for the fisherman is as follows: The time is noon, with the sun at zenith. The fisherman is 6 meters away from the water which has low waves on it with a radius of curvature of 6 meters. The hazard weighted irradiance is 8.20 microW/cm$^2$ which is far above the threshold for both solar retinitis and night vision loss. With a 550 cut-on filter, the irradiance drops to 0.045 microW/cm$^2$ which is below the threshold for solar retinitis but above the threshold for night vision loss. With the addition of the polarizer, the hazard weighted irradiance is reduced to 0.005 microW/cm$^2$ which is below the night vision loss threshold.

The most protective filter is the 550 cut-on. The 550 cut-on was selected as a limit because it is the greatest cut-on which does not interfere with red-green-yellow color discrimination which is needed for safety with traffic signals. This traffic signal recognition was determined experimentally. This lens is the one of choice for persons requiring the maximum protection such as those with diseased retinas i.e. Retinitis Pigmentosa, age-related macular degeneration etc. However, the lens may also be worn by others seeking maximum protection.

The typical situation for the police officer is as follows: The time is noon, with the sun at zenith. The driver is 5 meters away from the glass window of the car in front of it. The glass window has a radius of curvature of 4 meters. The hazard weighted irradiance is 39.60 microW/cm$^2$ which is far above the threshold for both solar retinitis and night vision loss. With a 450 cut-on filter, the irradiance drops somewhat, but because of the need for color verity by the officer to correctly identify the color of vehicles, the officer is above threshold for both the night vision loss threshold and the solar retinitis threshold. However, he is still better off than if he did not utilize the polarizing blue blocking lens.

The typical situation for the pilot is as follows: The time is noon, with the sun at zenith. The pilot is a highly variable distance from cloud cover which can change on short notice from overcast to brilliant sun. The state of polarization can also change dramatically depending upon the direction of the sun and the could conditions. For these reasons it is difficult to predict the hazard the pilot is exposed to. However, it is known that the pilot is exposed to far more intensity of overall blue and UV due to the altitude. (Atmosphere absorbs UV and blue light to some extent so persons at high altitude are at greater risk than those close to sea level.) A pilot may use any cut-on lens from 515 to 550 to mitigate the damage. The unexplained effect of this invention which allows them to be used over a wide range of light conditions will be of use to the pilot.

In general, for situations where the usage environment is well known and defined, the suggested cut-on can be determined by the quantitative methods described by equations [22] and [23]. In those situations where the usage environment is ill defined or highly variable, the suggested cut-on can be determined by the comfort of the user in a specific usage environment.

While the invention has been described in complete detail and pictorially shown in the accompanying drawings it is not to be limited to such details, since many changes and modification may be made to the invention without departing from the spirit and the scope thereof. For example, the inventive lens 10 also has application flight, ski and visors. Hence, it is described to cover any and all modifications and forms which may come within the language and scope of the claims.

We claim:

1. A lens for use in sunglasses adapted to block from incidence at a human eye selected wavelengths of sunlight that are harmful to the eye and to transmit to the eye selected wavelengths of visible sunlight that maintain color verity and allow for high visual acuity, comprising:
    a substantially transparent laminate having a light polarizing material; and
    a sharp cut-on filter associated with the laminate and adapted to block over ninety-nine percent of wavelengths of non-polarized light between 300 nm and about 450 nm and to transmit greater than 20 percent of wavelengths of polarized light greater than 625 nm, the filter further being adapted to commence sharply cutting on transmission of light at a sharp cut-on wavelength of between 450 nm and 550 nm and being characterized by a spectral transmission curve, a portion of whose slope at wavelengths of light greater than the cut-on wavelength but less than 650 nm rises more than 0.5 percent change in light transmission for every one nanometer of increasing wavelength change.

2. A lens for use in sunglasses according to claim 1, wherein the polarizing material is adapted to substantially horizontally polarize wavelengths of light.

3. A lens for use in sunglasses according to claim 1, wherein:
    the laminate includes two layers of optical plastic; and
    the light polarizing material is a film situated between the two layers.

4. A lens for use in sunglasses according to claim 1, wherein the plastic is composed of di-allyl glycol carbonate.

5. A lens for use in sunglasses according to claim 1, wherein the filter is composed of a combination of dispersed yellow dye 23 and dispersed orange dye 3 and is adapted to sharply cut-on transmission of light at a sharp cut-on wavelength of between 450 and 515 nm and has a spectral transmission curve whose slope at wavelengths greater than the cut-on wavelength but less than 650 nm rises more than 0.5 percent change in light transmission for every one nanometer of increasing wavelength change.

6. A lens for use in sunglasses according to claim 1, wherein the filter is composed of a combination of dispersed orange dye 3 and dispersed red dye 2 and is adapted to sharply cut-on transmission of light at a sharp cut-on wavelength of between 515 and 550 nm and has a spectral transmission curve whose slope at wavelengths greater than the cut-on wavelength but less than 650 nm rises more than 0.5 percent change in light transmission for every one nanometer of increasing wavelength change.

7. A lens for use in sunglasses according to claim 1, wherein the sharp cut-on filter transmits greater than percent 20 percent but not greater than 40 percent of wavelengths of polarized light greater than 625 nm.

8. A lens for use in sunglasses adapted to block from incidence at a human eye selected wavelengths of sunlight that are harmful to the eye and to transmit to the eye selected wavelengths of visible sunlight that maintain color verity and allow for high visual acuity, comprising:
    a substantially transparent laminate having a light polarizing material; and
    a sharp cut-on filter associated with the laminate and adapted to substantially block wavelengths of non-polarized light between 300 nm and about 450 nm and to commence sharply cutting-on transmission of light at a sharp cut-on wavelength of between 450 nm and 500 nm and being characterized by a spectral transmission curve, a portion of whose slope at wavelengths of light greater than the cut-on wavelength but less than 650 nm rises more than 0.5 percent change in light transmission for every one nanometer of increasing wavelength change.

9. A lens according to claim 8, wherein the sharp cut-on filter transmits between 20 and 40 percent of wavelengths of polarized light greater than 625 nm.

10. A lens according to claim 8, wherein the polarizing material is adapted to substantially horizontally polarize wavelengths of light.

11. A lens according to claim 8, wherein:
    the laminate includes two layers of optical plastic; and
    the light polarizing material is a film situated between the two layers.

12. A lens according to claim 11, wherein the plastic is composed of di-allyl glycol carbonate.

13. A lens according to claim 8, wherein the filter is further adapted to transmit at least 20 percent of wavelengths of polarized light greater than 625 nm.

14. A lens according to claim 8, wherein the filter is further adapted to transmit at least 30 percent of wavelengths of polarized light greater than 625 nm.

15. A lens according to claim 8, wherein the filter is further adapted to transmit between 10 and 90 percent of wavelengths of light greater than 625 nm.

16. A lens according to claim 7, wherein the filter is composed of a combination of dispersed yellow dye 23 and dispersed orange dye 3 and is adapted to sharply cut-on transmission of light at a sharp cut-on wavelength of between 450 and 500 nm and has a spectral transmission curve whose slope at wavelengths greater than the cut-on wavelength but less than 650 nm rises more than 0.5 percent change in light transmission for every one nanometer of increasing wavelength change.

* * * * *

UNITED STATES PATENT AND TRADEMARK OFFICE
CERTIFICATE OF CORRECTION

PATENT NO. : 5,177,509

DATED : January 5, 1993

INVENTOR(S) : Laurie A. Johansen et al

It is certified that error appears in the above-identified patent and that said Letters Patent is hereby corrected as shown below:

In column 14, line 57, change "micro W/cm2" to --microW/cm2--.

In column 17, line 59, change "dying" to --dyeing--.

In column 17, line 66, change "dying" to --dyeing--.

In column 18, line 17, change "dying" to --dyeing--.

In column 19, line 37, change "dying" to --dyeing--.

In column 22, line 58, change "could" to --cold--.

In column 23, line 14, change "flight, ski and visors" to --flight and ski goggles and visors--.

In column 23, line 49, change "claim 1" to --claim 3--.

UNITED STATES PATENT AND TRADEMARK OFFICE
CERTIFICATE OF CORRECTION

PATENT NO. : 5,177,509

DATED : January 5, 1993

INVENTOR(S) : Laurie A. Johansen, et al

It is certified that error appears in the above-indentified patent and that said Letters Patent is hereby corrected as shown below:

Column 24, line 54, change "claim 7" to —claim 8—

Signed and Sealed this

Tenth Day of January, 1995

Attest:

BRUCE LEHMAN

Attesting Officer

Commissioner of Patents and Trademarks